United States Patent [19]

Child et al.

[11] Patent Number: 5,073,665

[45] Date of Patent: * Dec. 17, 1991

[54] PROCESS FOR ALKYLATING OLEFINS AND ISOPARAFFINS IN A FIXED BED REACTOR

[75] Inventors: Jonathan E. Child, Sewell, N.J.; Albin Huss, Jr., Chadds Ford, Pa.; Frederick J. Krambeck, Cherry Hill, N.J.; Francis P. Ragonese, Cherry Hill, N.J.; Robert T. Thomson, Voorhees, N.J.; Sergei Yurchak, Media, Pa.

[73] Assignee: Mobil Oil Corp., Fairfax, Va.

[*] Notice: The portion of the term of this patent subsequent to Feb. 12, 2008 has been disclaimed.

[21] Appl. No.: 560,397

[22] Filed: Jul. 31, 1990

[51] Int. Cl.$^5$ .............................................. C07C 2/58
[52] U.S. Cl. .................................................... 585/722
[58] Field of Search ................ 585/722, 716, 727, 728

[56] References Cited

U.S. PATENT DOCUMENTS

| | | | |
|---|---|---|---|
| 3,251,902 | 5/1966 | Garwood et al. | 260/683 |
| 3,450,644 | 6/1969 | Lanewala et al. | 252/416 |
| 3,549,557 | 12/1970 | Bolton et al. | 252/455 |
| 3,624,173 | 11/1971 | Kirsch et al. | 260/671 |
| 3,644,565 | 2/1972 | Biale | 260/683 |
| 3,647,916 | 3/1972 | Caesar et al. | 260/683 |
| 3,655,813 | 4/1972 | Kirsch et al. | 260/683 |
| 3,706,814 | 12/1972 | Kirsch et al. | 260/683 |
| 3,738,977 | 6/1973 | Biale | 260/94.9 |
| 3,855,342 | 12/1974 | Huang et al. | 260/683 |
| 3,862,258 | 1/1975 | Huang et al. | 260/683 |
| 3,893,942 | 7/1975 | Yang | 252/411 |
| 3,917,738 | 11/1975 | Fenske et al. | 260/683 |
| 4,384,161 | 5/1983 | Huang | 585/727 |
| 4,439,409 | 3/1984 | Puppe et al. | 423/328 |
| 4,826,667 | 5/1989 | Zones et al. | 423/277 |
| 4,918,255 | 4/1990 | Chou et al. | 585/728 |
| 4,926,616 | 2/1991 | Chou et al. | 585/728 |
| 4,992,615 | 2/1991 | Huss, Jr. et al. | 585/722 |
| 5,012,033 | 4/1991 | Child et al. | 585/722 |

FOREIGN PATENT DOCUMENTS 0231860 1/1986 European Pat. Off. .
0293032 11/1988 European Pat. Off. .

*Primary Examiner*—Anthony McFarlane
*Attorney, Agent, or Firm*—Alexander J. McKillop; Charles J. Speciale; Dennis P. Santini

[57] ABSTRACT

A process for alkylation of isoparaffins and olefins employing a fixed bed of catalyst. The catalyst composition includes an unpromoted synthetic zeolite. The alkylate product contains highly branched paraffins and has an octane suitable for blending into motor gasolines. Alternatively multiple fixed beds can be employed with direct effluent recycle or split olefin feeds.

21 Claims, 2 Drawing Sheets

PROCESS FOR ALKYLATING OLEFINS AND ISOPARAFFINS IN A FIXED BED REACTOR

CROSS-REFERENCE TO RELATED APPLICATIONS

This application is related by subject matter to U.S. patent application Ser. No. 254,524 filed Oct. 6, 1988, now U.S. Pat. No. 4,954, which is a continuation-in-part of U.S. patent application Ser. No. 98,176, filed Sept. 18, 1987, now abandoned, which is a continuation-in-part of U.S. patent application Ser. No. 890,268 filed July 29, 1986, now abandoned. This application is also related by subject matter to commonly assigned copending applications 07/470,016 and 07/470,014, both filed on Jan. 25, 1990, now U.S. Pats. No. 5,012,033 and No. 4,992,615 respectively.

BACKGROUND OF THE INVENTION

The present invention relates to a isoparaffin-olefin alkylation process employing, as catalyst, a non-promoted zeolite of a particular type to provide an alkylate product useful, inter alia, as an octane enhancer for gasoline.

As a result of the curtailment in the use of tetraethyl lead as an octane-improving additive for gasoline, not only has the production of unleaded gasoline increased but the octane number specification of all grades of gasoline have increased as well. Isoparaffin-light olefin alkylation plays an important role in the manufacture of high octane gasoline blending stocks with alkylate typically comprising 10-15% of the gasoline pool. Alkylate is an especially valuable component of the gasoline pool as it possesses both high research and motor octane (low sensitivity) numbers, contains no olefins or aromatics and little or no sulfur, demonstrates excellent stability and is clean burning.

Alkylation involves the addition of an alkyl group to an organic molecule. Thus, an isoparaffin can be reacted with an olefin to provide an isoparaffin of higher molecular weight Industrially, alkylation often involves the reaction of $C_2$-$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88-94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alkylation process based on a solid catalyst system.

The alkylation process of U.S. Pat. No. 3,862,258 utilizes a catalyst comprising a macroreticular acid cation exchange resin and boron trifluoride. It is reported in this patent that the life of such a catalyst can be extended by the presence in the reaction mixture of closely controlled amounts of water which can be added to the feed as water or as a water-producing compound, for example, in the form of an alcohol such as methanol.

U.S. Pat. No. 3,855,342 also discloses the use of a combination of a macroreticular acid cation exchange resin and boron trifluoride as an isoparaffin-olefin alkylation catalyst. the boron trifluoride component is present in an amount sufficient to saturate the cation exchange resin component of the catalyst system.

Crystalline metallosilicates, or zeolites, have also been widely investigated for use in the catalysis of isoparaffin alkylation. For example, U.S. Pat. No. 3,251,902 describes the use of a fixed bed of ion exchanged cystalline aluminosilicate having a reduced number of available acid sites for the liquid phase alkylation of $C_4$-$C_{20}$ branched-chain paraffins with $C_2$-$C_{12}$ olefins. The patent further discloses that the $C_4$-$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$-$C_3$ olefins using certain crystalline aluminosilicate zeolite catalysts in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin alkylation process employing, as catalyst, a Group VIII metal-containing zeolite which is periodically hydrogenated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide promoters, etc.

U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalysts having been pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,384,161 describes a process of alkylating isoparaffins with olefins to provide alkylate employing as catalyst a large pore zeolite capable of absorbing 2,2,4-trimethlpentane, e.g., ZSM-4, ZSM-29, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

Isoparaffin-olefin alkylation is generally carried out in stirred tank or riser type reactors Such reactors are more expensive to build and operate than fixed bed reactors. Accordingly, it is preferable to carry out isoparaffin-olefin alkylation in a fixed bed reactor as opposed to using a stirred tank or riser-type reactor. However, up to now it has not been possible to obtain satisfactory alkylate yields in a fixed bed reactor.

SUMMARY OF THE INVENTION

Figure 1:
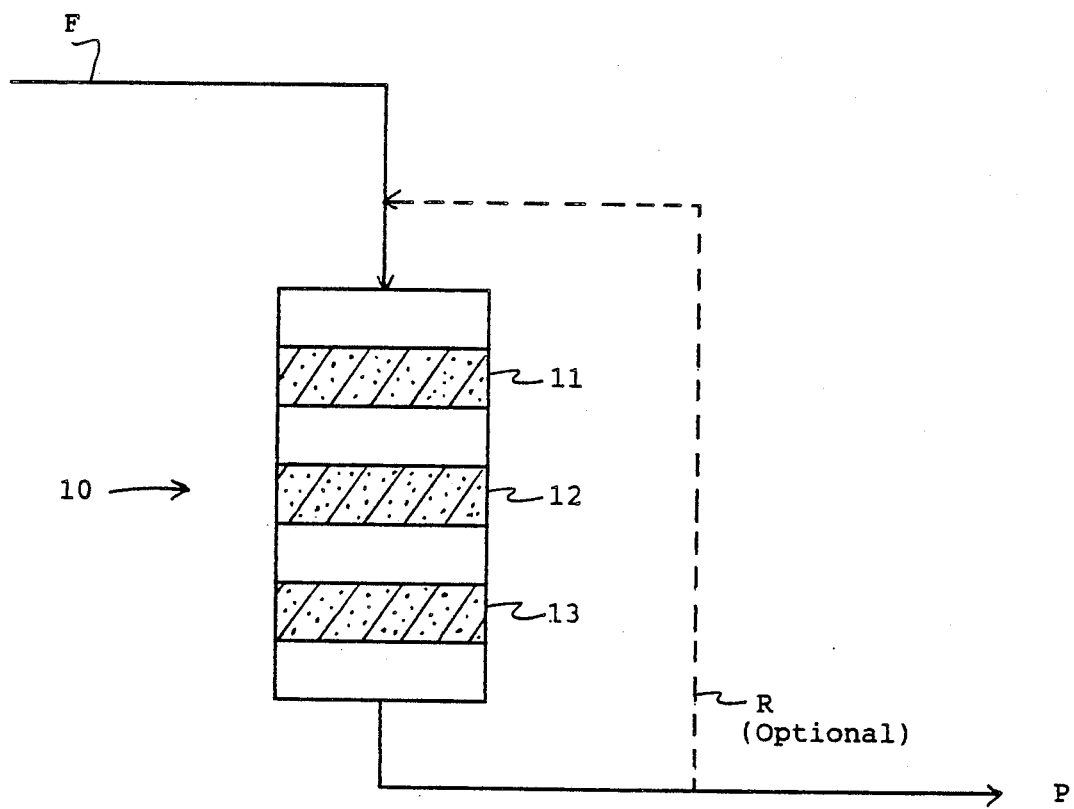
FIG. 1 is a flow diagram illustrating the process of the present invention with a three-bed reactor and optional recycle stream.

In accordance with the present invention, isoparaffin-olefin alkylation is carried out in a fixed bed of catalyst particles. The catalyst is a synthetic porous crystalline material, i.e. a zeolite, which is unpromoted by a Lewis acid and which is characterized by an x-ray diffraction pattern including values substantially as set forth in Tables A to D, infra. This catalyst offers the refiner a more environmentally acceptable process than the currently used hydrofluoric and sulfuric acid alkylation processes.

When used under the fixed bed reaction conditions of this invention, unpromoted zeolite MCM-22 provides an alkylation operation of considerable technical and economical efficiency. The alkylate produced by the process of this invention is of high quality based on both research and motor octane numbers and as such is particularly well suited for blending into the gasoline pool.

DETAILED DESCRIPTION OF THE PREFERRED EMBODIMENTS

The feedstock of the alkylation process of the present invention includes at least one olefin.

Isoparaffin compounds suitable for use herein include branched chain paraffinic hydrocarbons possessing from 1 to 20 carbon atoms, preferably about 4 to 8 carbon atoms as, for example, isobutane, 3-methylhexane, 2-methylbutane, 2,3-dimethylbutane, and 2,4-dimethylhexane.

The olefin reactant employed herein generally contains from 2 to about 12 carbon atoms. Representative examples include ethylene, propylene, 1-butene, 2-butene, isobutylene, pentenes, hexenes, heptenes, and octenes. Particularly preferred are $C_3$ and $C_4$ olefins, and mixtures thereof.

In general, the overall mole ratio of total isoparaffin to total olefin in the combined hydrocarbon feed can be from about 0.1:1 to about 500:1, preferably in the range of from about 3:1 to about 50:1, and still more preferably in the range of from about 5:1 to about 15:1.

The reactants can be introduced to the alkylation reaction zone together with one or more other materials which serve to enhance the overall conversion operation. Thus, for example, relatively small quantities of hydrogen and/or hydrogen donors can be present in the reaction zone to suppress catalyst aging. Water and/or materials such as alcohols which provide water under the alkylation conditions selected can also be introduced into the reaction zone for this purpose. Oxygen and/or other materials which tend to suppress oligomerization of the olefin feed can be present in the typically very small amounts which are effective to achieve this benefit. The optimum amounts of these optional materials which can be utilized to advantage in a particular alkylation operation can be readily determined by those skilled in the art employing routine experimentation.

The operating temperature of the alkylation process herein can extend over a fairly broad range, e.g., from about $-25°$ ($-13°$ F.) to about 400° C. (752° F.), and is preferably within the range of from about 75° C. (167° F.) to about 200° C. (392° F). The practical upper operating temperature will often be dictated by the need to avoid an undue occurrence of undesirable side reactions.

The pressures employed in the present process can extend over a considerably wide range, e.g., from subatmospheric pressure to about 5000 psig, preferably from atmospheric pressure to about 1000 psig, and more preferably from about 500 to 700 psig.

The amount of zeolite catalyst used in the present alkylation process can be varied over relatively wide limits. In general, the amount of zeolite as measured by the weight hourly space velocity (WHSV) based on olefin can range from about 0.01 $hr^{-1}$ to about 100 $hr^{-1}$ preferably from about 0.05 $hr^{-1}$ to 10.0 $hr^{-1}$. It will, of course, be realized by those skilled in the art that the amount of catalyst selected for a particular reaction will be determined by several variables including the reactants involved as well as the nature of the catalyst and the operating conditions employed.

The alkylation catalyst is used without a Lewis acid promoter. A Lewis acid is generally considered to be a molecule which is capable of combining with another molecule or ion by forming a covalent chemical bond with two electrons from the second molecule or ion, which is to say, a Lewis acid is an electron acceptor. Examples of Lewis acids include boron trifluoride ($BF_3$), antimony pentafluoride ($SbF_5$) and aluminum chloride ($AlCl_3$). Other Lewis acids are disclosed in "Friedel-Crafts and Related Reactions", Interscience Publishers, Chapters III and IV (1963), the contents of which are incorporated by reference herein.

The alkylation reactor for use in the process of the present invention can employ single or multiple fixed beds of catalyst. As previously stated, fixed bed reactors are preferable to stirred tank or riser type reactors, the latter two having found wide use in alkylation operations employing the older catalysts such as hydrofluoric acid, sulfuric acid, and the like. Fixed bed reactors are less expensive to build and operate, and easier to scale up.

In fixed bed reactors the olefin concentration at the inlet of the reactor is higher than at the outlet. To maximize yield and product quality, it is desirable to operate at low temperature where the olefin concentration is relative high, and at higher temperature where the olefin concentration is relatively low. This can be accomplished by operating several fixed beds in series where the effluent from each reactor is heated prior to being fed to the next reactor. Conventional furnaces, heat exchangers, or the addition of hot reactants or inerts can be used to heat the effluents.

In one embodiment of the process of the present invention, reactor effluent is recycled to increase the ratio of isoparaffin to olefin. This produces a higher yield of high octane alkylate.

In order to prevent the degradation of product quality, prior known processes required the isoparaffin to be separated from the product. For example, in U.S. Pat. No. 2,843,642, which describes a process for the alkylation of isobutane, a fractionator is employed to separate isobutane before it is recycled to the reactor.

In the process of the present invention, however, a portion of the reactor effluent can be recycled to the reactor(s) without fractionation as illustrated in FIG. 1 wherein the optional recycle stream R is a direct effluent pumparound. Nevertheless there is no significant degradation of product quality. Thus, employment of the zeolite described below as an alkylation catalyst permits the elimination of the fractionation step in the recycle loop, thereby significantly reducing the operating cost of the overall process.

Figure 2:
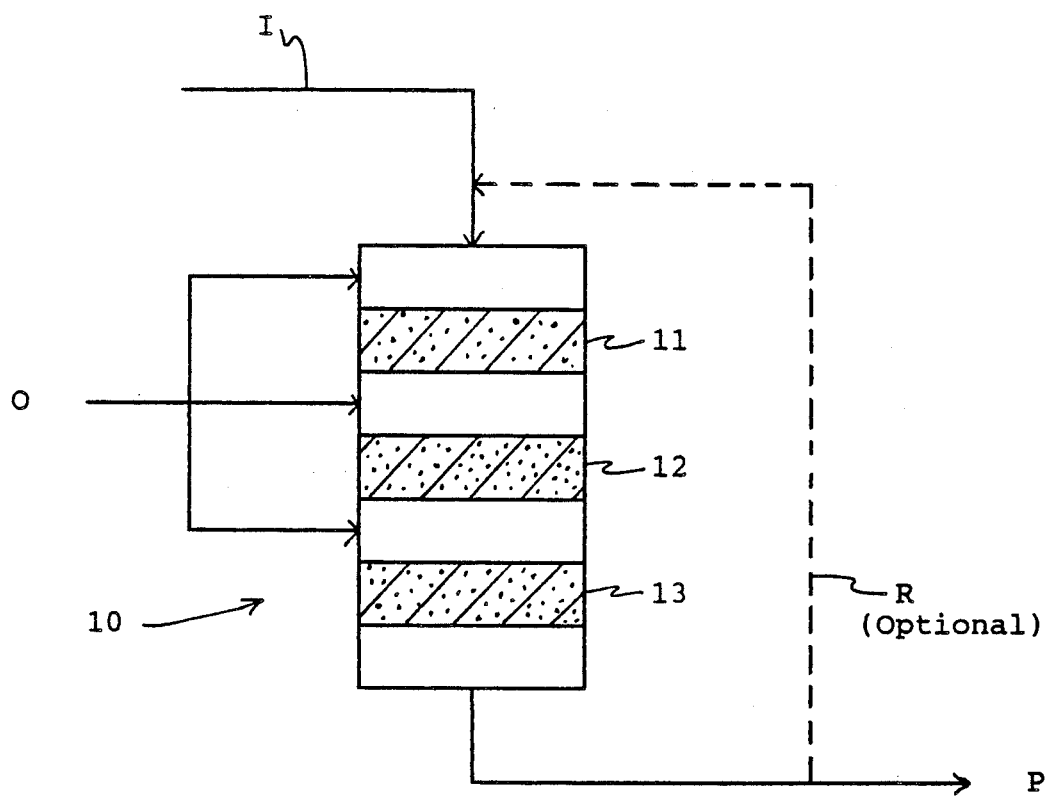
FIG. 2 is a flow diagram illustrating an embodiment of the present invention employing a split olefin feed.

In yet another embodiment of the present invention the olefin feed can be split into two or more streams as illustrated in FIG. 2, each stream being introduced into a different part of the reactor. For example, in a series of fixed bed reactors, a portion of the divided stream can be introduced into each reactor bed. This provides a high isoparaffin/olefin ratio in each reactor.

The catalyst particles employed in the process of the present invention are typically provided as composites of the zeolite and a binder, e.g., alumina.

In its calcined form, the zeolite used for the catalystic process described herein is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form of zeolite may be characterized by an x-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, the zeolite may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |

TABLE D-continued

| Interplanar d-Spacing (A) | Relative Intensity, $I/I_o \times 100$ |
|---|---|
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of this zeolite. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 compositions of U.S. Pat. No. 4,439,409, incorporated herein by reference, and the crystalline material of U.S. application Ser. No. 254,524, incorporated herein by reference, referred to herein as "MCM-22".

Zeolite MCM-22 has a composition involving the molar relationship:

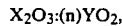

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

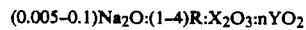

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred cations are those which tailor the activity of the catalyst. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use in the catalyst composition herein, the synthetic porous crystalline material zeolite should be subjected to thermal treatment to remove part or all of any organic constituent present therein.

The zeolite present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal temperature can be performed at a temperature of up to about 925° C.

Prior to its use in the catalyst composition and process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30. wt.% solid $YO_2$. Where $YO_2$ is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desirable to incorporate the zeolite crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitable serve as diluents to control the amount of conversion so that products can be obtained economically and in a controlled fashion without having to employ other means for controlling the rate of reaction. These materials can be incorporated into naturally occurring clays, e.g., bentonite and kaolin, to improve the crush strength of the catalyst under commercial operating conditions. Good crush strength is an advantageous attribute for commercial use since it prevents or delays breaking down of the catalyst into powder-like materials. Said materials, i.e., clays, oxides, etc., function as binders for the catalyst. Clay binders have been employed normally only for the purpose of improving the crush strength of the catalyst.

Naturally occurring clays which can be composited with the zeolite crystals include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the zeolite crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 90 percent by weight and more usually, particularly when the composite is prepared in the form of beads, in the range of about 2 to about 80 weight percent of the composite.

The stability of zeolite MCM-22 may be increased by steaming. U.S. Pat. Nos. 4,663,492; 4,594,146; 4,522,929; and, 4,429,176, the entire disclosures of which are incorporated herein by reference, describe conditions for the steam stabilization of zeolite catalysts which can be utilized to steam-stabilize the catalyst for use herein. The steam stabilization conditions include contacting the catalyst with, e.g., 5–100% steam at a temperature of at least about 300° C. (e.g., 300°–650° C.) for at least one hour (e.g., 1–200 hours) at a pressure of 101–2,500 kPa. In a more particular embodiment, the catalyst can be made to under steaming with 75-100% steam at 315°-500° C. and atmospheric pressure for 2-25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

In order to more fully illustrate the process of this invention and the manner of practicing same, the following examples are presented. Whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample g/100 g of calcined adsorbant. Zeolite MCM-22 always exhibits Equilibrium Adsorption values of greater than about 10 wt.% for water vapor, greater than about 4.5 wt.%, usually greater than about 7 wt.% for cyclohexane vapor, and greater than about 10 wt.% for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$).

The Alpha Test is described in U.S. Pat. No. 3,354,078; in the *Journal of Catalysis*, vol. 4, p. 527 (1965); vol, 6, p. 278 (1966); and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

EXAMPLE 1

One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (90% $SiO_2$).

The reaction mixture had the following composition, in mole ratios:
$SiO_2/Al_2O_3 = 30.0$
$OH^-/SiO_2 = 0.18$
$H_2O/SiO_2 = 44.9$
$Na/SiO_2 = 0.18$
$R/SiO_2 = 0.35$
where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

$H_2O$: 15.2 wt.%
Cyclohexane: 14.6 wt.%
n-Hexane: 16.7 wt.%

The surface area of the zeolite was measured to be 494 $m^2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio | 21.10 |

TABLE E

| Degrees 2-Theta | Interplanar d-Spacing (A) | $I/I^o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| | Example | | |
|---|---|---|---|
| | 3 | 4 | 5 |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a larger preparation of the required zeolite 1200 g of hexamethyleneimine was added to a solution containing 268 g of sodium aluminate, 267 g of 50% NaOH solution and 11,800 g of $H_2O$. To the combined solution was added 2,280 g of Ultrasil silica. The mixture was crystallized with agitation (about 200 rpm) at 145° C. in a 5 gallon reactor. Crystallization time was 59 hours. The product was water washed and dried at Product chemical composition (uncalcined), surface area and adsorption analyses results were as set forth in Table G:

TABLE G

| Product Composition | | |
|---|---|---|
| C | 12.1 | wt. % |
| N | 1.98 | wt. % |
| Na | 640 | ppm |
| $Al_2O_3$ | 5.0 | wt. % |
| $SiO_2$ | 74.9 | wt. % |
| $SiO_2/Al_2O_3$, mole ratio | 25.4 | |
| Adsorption, wt. % | | |
| Cyclohexane | 9.1 | |
| n-Hexane | 14.9 | |
| $H_2O$ | 16.8 | |
| Surface Area, $m^2/g$ | 479 | |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material ion-exchanged 100 ml of 0.1N TEABr, TPABr and $LaCl_3$ solution separately. Each exchange was carried out at ambient temperature for 24 hours and repeated three times The exchanged samples were collected by filtration, water-washed to be halide-free and dried. The compositions of the exchanged samples are tabulated below demonstrating the exchange capacity of the present crystalline silicate for different ions.

| | Ionic Composition, wt. % | | |
|---|---|---|---|
| Exchange Ions | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:
$SiO_2/B_2O_3 := 6.1$
$OH^-/SiO_2 := 0.06$
$H_2O/SiO_2 := 19.0$
$K/SiO_2 := 0.06$
$R/SiO_2 := 0.30$ where R is hexamethyleneimine. The mixture was crystallized in a stainless steel reactor, with agitation, at 150° C. for 8 days. The crystalline product was filtered, washed with water and dried at 120° C. A portion of the product was calcined for 6 hours at 240° C. and found to have the following sorption capacities:
$H_2O$ (12 Torr): 11.7 wt.%
Cyclohexane (40 Torr): 7.5 wt.% n-Hexane (40 Torr): 11.4 wt.%

The surface area of the calcined crystalline material was measured (BET) to be 405 m²/g.

The chemical composition of the uncalcined material was determined to be as follows:

| N | 1.94 wt. % |
|---|---|
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al+B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_2/B_2O_3 = 12.3$
$OH^-//SiO_2 = 0.056$
$H_2O/Sio_2 = 18.6$
$K/SiO_2 = 0.056$
$R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

$H_2O$: 14.4 wt.%
Cyclohexane: 4.6 wt.%
n-Hexane 14.0 wt.%

The surface area of the calcined crystalline material was measured to be 438m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al+B)_2O_3$, molar ratio | 28.2 |

EXAMPLE 14

A portion of the calcined crystalline product of Example 13 was tested in the Alpha Test and found to have an Alpha Value of 5.

EXAMPLE 15

A sample of MCM-22 was prepared according to the procedure of Example 1 and then calcined at 1000° F. in flowing air.

EXAMPLE 16

Referring to FIG. 1, a reactor 10 containing three fixed beds 11, 12, 13 of the catalyst of Example 15, was provided for the alkylation process of the present invention. A feedstock F containing isobutane and 1-butene in a 10/1 mole ratio (isobutane/1-butene) was contacted with the catalyst beds in series under alkylation conditions to produce an alkylate product P. The inlet temperature of the second and third beds 12, and 13 respectively, exceeded the outlet temperatures of the respective preceding bed. In this example the optional recycle stream R was not employed. Table H below sets forth the process conditions and results of this example. The yield is defined as the ratio of the weight of $C_5+$ products per weight of olefin converted.

TABLE H

| Alkylation Employing Unpromoted MCM-22 Under Fixed-Bed Conditions Without Recycle (10/1 Isobutane/1-Butene Mole Ratio) | |
|---|---|
| Time on Stream, Hrs. | 288 |
| Inlet Temperatures, °F. | |
| Bed 1 | 250 |
| Bed 2 | 325 |
| Bed 3 | 350 |
| Pressure, psig | 650 |
| Olefin WHSV, $Hr^{-1}$ | 0.063 |
| Recycle Ratio | 0 |
| Olefin Conversion, wt % | 93 |
| $C_5+$ Products, wt % | |
| $C_5$'s–$C_7$'s | 28 |
| $C_8$'s | 54 |
| $C_9+$ | 18 |
| TMP/DMH | 1.5 |
| Yield | 1.3 |

As can be seen from Table H, a 93% olefin conversion is achieved under these circumstances. The alkylate product of this example contained 54 wt. % of $C_8$ hydrocarbon compounds. The mole ratio of trimethylpentane to dimethylhexane (TMP/DMH) in the alkylate product was 1.5.

EXAMPLE 17

Example 17 was carried out in a three bed reactor as shown in FIG. 1. Unlike Example 16, however, recycle stream R was employed, i.e. a portion of the product stream P was diverted and reintroduced directly into feedstock stream F without an intermediate fractionation step. Example 17 employed a 4/1 series of recycle to fresh feed. Operating conditions are set forth in Table I below.

TABLE I

| Alkylation Employing Unpromoted MCM-22 Under Fixed-Bed Conditions With Recycle (10/1 Isobutane/1-Butene Mole Ratio) | |
|---|---|
| Time on Stream, Hrs. | 404 |
| Inlet Temperatures, °F. | |
| Bed 1 | 325 |
| Bed 2 | 350 |
| Bed 3 | 375 |
| Pressure, psig | 650 |
| Olefin WHSV, $Hr^{-1}$ | 0.064 |
| Recycle Ratio | 4 |
| Olefin Conversion, wt % | 89 |

TABLE I-continued

Alkylation Employing Unpromoted MCM-22 Under
Fixed-Bed Conditions With Recycle
(10/1 Isobutane/1-Butene Mole Ratio)

| $C_5+$ Products, wt % | |
|---|---|
| $C_5$'s–$C_7$'s | 23 |
| $C_8$'s | 61 |
| $C_9+$ | 16 |
| TMP/DMH | 1.3 |
| Yield, g $C_5+$/g olefin converted | 1.5 |

As can be seen from Table I, an olefin conversion of 89% is achieved under these circumstances. The product distribution includes 61% of $C_8$'s, which is significantly higher than the percentage of $C_8$'s produced without recycling. Furthermore, recycling enables one to achieve a yield ratio of 1.5, as opposed to a yield ratio of 1.3 without recycling.

EXAMPLE 18

Prophetic Example 18 is carried out in a 3 bed reactor as shown in FIG. 2. Unlike Examples 16 and 17, the feedstock components, isobutane and 1-butene, are introduced separately into the reactor. The isobutane is introduced via stream I as shown in FIG. 2. The olefin, 1-butene, is introduced via stream O which is split such that a portion of the olefin is introduced to each of the three stages. Recycle is employed in this example. Product is drawn off as indicated by stream P. Operating conditions and results are set forth in Table J below, based on calculated results.

TABLE J

Alkylation Employing Unpromoted MCM-22 Under
Fixed-Bed Conditions Using Split Olefin Feed
(10/1 Isobutane/1-Butene Mole Ratio)

| Time on Stream, Hrs. | 400 |
|---|---|
| Inlet Temperatures, °F. | |
| Bed 1 | 325 |
| Bed 2 | 350 |
| Bed 3 | 375 |
| Pressure, psig | 650 |
| Olefin WHSV, Hr$^{-1}$ | 0.064 |
| Recycle Ratio | 4 |
| Olefin Conversion, wt % | 85 |
| $C_5+$ Products, wt % | |
| $C_5$'s–$C_7$'s | 20 |
| $C_8$'s | 68 |
| $C_9+$ | 12 |
| TMP/DMH | 1.3 |
| Estimated Yield, g $C_5+$/g olefin converted | 1.7 |

What is claimed is:

1. A process for producing an alkylate product from a feedstock containing at least one isoparaffin and at least one olefin, said process comprising contacting said feedstock under alkylation reaction conditions with at least one fixed bed of catalyst composition, said catalyst composition comprising a synthetic zeolite which is unpromoted by a Lewis acid and which is characterized by an X-ray diffraction pattern including values substantially as follows:

| Interplanar d-Spacing (A) | Relative Intensity, $I/I° \times 100$ |
|---|---|
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | M–M |
| 4.06 ± 0.07 | W–S |
| 3.91 ± 0.07 | M–VS |
| 3.42 ± 0.06 | VS |

2. The process of claim 1 wherein said zeolite is characterized by an X-ray diffraction pattern including values substantially as follows:

| Interplanar d-Spacing (A) | Relative Intensity, $I/I° \times 100$ |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

3. The process of claim 1 wherein the zeolite is characterized by an X-ray diffraction pattern including values substantially as follows:

| Interplanar d-Spacing (A) | Relative Intensity, $I/I° \times 100$ |
|---|---|
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |
| 4.10 ± 0.07 | W–S |
| 4.06 ± 0.07 | W–S |
| 3.91 ± 0.07 | M–VS |
| 3.75 ± 0.06 | W–M |
| 3.56 ± 0.06 | W–M |
| 3.42 ± 0.06 | VS |
| 3.30 ± 0.05 | W–M |
| 3.20 ± 0.05 | W–M |
| 3.14 ± 0.05 | W–M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

4. The process of claim 1 wherein the zeolite is characterized by an X-ray diffraction pattern including values substantially as follows:

| Interplanar d-Spacing (A) | Relative Intensity, $I/I° \times 100$ |
|---|---|
| 30.0 ± 2.2 | W–M |
| 22.1 ± 1.3 | W |
| 12.36 ± 0.4 | M–VS |
| 11.03 ± 0.2 | M–S |
| 8.83 ± 0.14 | M–VS |
| 6.86 ± 0.14 | W–M |
| 6.18 ± 0.12 | M–VS |
| 6.00 ± 0.10 | W–M |
| 5.54 ± 0.10 | W–M |
| 4.92 ± 0.09 | W |
| 4.64 ± 0.08 | W |
| 4.41 ± 0.08 | W–M |
| 4.25 ± 0.08 | W |

-continued

| Interplanar d-Spacing (A) | Relative Intensity, $I/I^0 \times 100$ |
|---|---|
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

5. The process of claim 1 wherein the synthetic zeolite has a composition comprising the molar relationship:

$$X_2O_3:(n)YO_2$$

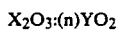

wherein X is a trivalent element selected from the group consisting of aluminum, boron, iron and gallium, Y is a tetravalent element selected from the group consisting of silicon and germanium, and n is at least 10.

6. The process of claim 1 wherein said synthetic zeolite has been treated to replace original cations, at least in part, with a cation or mixture of cations selected from the group consisting of hydrogen, rare earth metals, and metals of Groups IIA, IIIA, IVA, IB, IIB, IIIB, IVB, VIB and VIII of the Periodic Table.

7. The process of claim 1 wherein said synthetic zeolite has been thermally treated at a temperature of up to about 925° C.

8. The process of claim 1 wherein said zeolite possesses equilibrium adsorption values of greater than about 10 weight percent for water vapor, greater than about 4.5 weight percent for cyclohexane vapor, and greater than about 10 weight percent for n-hexane vapor.

9. The process of claim 1 wherein said isoparaffin is selected form the group consisting of isobutane, 3-methylhexane, 2-methylbutane, 2,3-dimethylbutane, 2,4-dimethylhexane, and mixtures thereof.

10. The process of claim 1 wherein said olefin is selected form the group consisting of ethylene, propylene, 1-butene, 2-butene, isobutylene, pentenes, hexenes, heptenes, octenes, and mixtures thereof.

11. The process of claim 1 wherein the mole ratio of isoparaffin to olefin in the feedstock is from 0.1:1 to about 500:1.

12. The process of claim 1 wherein the mole ratio of isoparaffin to olefin in the feedstock is from about 3:1 to 50:1.

13. The process of claim 1 wherein the mole ratio of isoparaffin to olefin in the feedstock is from about 5:1 to about 15:1.

14. The process of claim 1 wherein said alkylation reaction conditions include a temperature of from about −25° C. to about 400° C., a pressure of atmospheric pressure to about 1000 psig, and a space velocity of from about 0.01 hr$^{-1}$ WHSV to about 100 hr$^{-1}$ WHSV.

15. The process of claim 1 wherein said alkylation reaction conditions include a temperature of from about 75° C. to about 200° C., a pressure of from about 500 to 700 psig, and a space velocity of from about 0.05 hr$^{-1}$ WHSV to about 10.0 hr$^{-1}$ WHSV.

16. The process of claim 1 wherein said alkylation reaction is conducted with a plurality of fixed beds of catalyst.

17. The process of claim 1 wherein said isoparaffin and olefin components of the feedstock are separately introduced to the alkylation reaction, and said olefin component being divided into a plurality of olefin streams each stream being introduced to a separate fixed bed.

18. The process of claim 1 wherein at least a portion of said alkylate product is recycled with the feedstock.

19. The process of claim 1 wherein said process achieves an olefin conversion of at least 89%.

20. The process of claim 1 wherein said catalyst composition includes a matrix material.

21. The process of claim 20 wherein said matrix material is selected from the group consisting of silica, alumina, zirconia, titania, magnesia, beryllia, thoria, and combinations thereof.

* * * * *